United States Patent
Pace et al.

(10) Patent No.: US 6,462,820 B1
(45) Date of Patent: *Oct. 8, 2002

(54) OPERATOR-FREE FABRIC WEB INSPECTION SYSTEM

(75) Inventors: Edmund L. Pace, Pfafftown; Glenn R. Pierce, Winston-Salem; John R. Everhart, Winston-Salem; David L. Kamp, Winston-Salem; Jimmy F. Plyler, Salisbury; Dennis Starnes, Concord; James Moore Schenck, Winston-Salem; George S. Noonkester, King, all of NC (US)

(73) Assignee: Sara Lee Corporation, Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/805,352

(22) Filed: Mar. 13, 2001

Related U.S. Application Data

(63) Continuation of application No. 09/259,461, filed on Mar. 1, 1999, now Pat. No. 6,259,526.

(51) Int. Cl.[7] .......................... G01N 21/84; G01N 21/88
(52) U.S. Cl. ................... 356/430; 356/431; 356/238.2; 356/238.3
(58) Field of Search ................ 356/430, 431, 356/238.1, 238.2, 238.3; 226/11, 43, 45, 118.1, 180; 26/70, 77

(56) References Cited

U.S. PATENT DOCUMENTS

| | | | | |
|---|---|---|---|---|
| 3,721,376 A | * | 3/1973 | Christian et al. | 226/42 |
| 5,437,082 A | * | 8/1995 | Maenaka | 28/190 |
| 5,440,648 A | * | 8/1995 | Roberts et al. | 356/430 |
| 6,259,526 B1 | * | 7/2001 | Pace et al. | 356/430 |

* cited by examiner

Primary Examiner—F. L. Evans
Assistant Examiner—Zandra Smith
(74) Attorney, Agent, or Firm—Womble Carlyle Sandridge & Rice, PLLC

(57) ABSTRACT

A moving fabric web vision inspection system. The apparatus includes at least two electronic cameras on one side of the moving fabric web for measuring the light intensity of a predetermined area of the moving fabric web. A high frequency, backlight, contrast panel on the other side of the moving fabric web provides reference point for the cameras to detect a defect. A controller connected to each of the electronic cameras generates a stop signal if the light intensity of the predetermined area of the moving fabric web deviates from a predetermined value. The predetermined value corresponds to a detected defect in the moving fabric web. Finally, a repair station downstream from the cameras allows an operator to repair a defect detected by the vision inspection system.

10 Claims, 4 Drawing Sheets

OPERATOR-FREE FABRIC WEB INSPECTION SYSTEM

RELATED APPLICATIONS

This is a continuation of application Ser. No. 09/259,461 filed on March 1, 1999, now U.S. Pat. No. 6,259,526.

BACKGROUND OF THE INVENTION

1. Field of the Invention

The present invention relates generally to fabric inspection systems and, more particularly, to an apparatus for inspecting a tubular knitted fabric web at high speed without operator intervention.

2. Description of the Prior Art

In the manufacture of apparel, particularly T-shirts and the like, after the greige goods have been knit they are inspected and transferred to a finishing line. Inspection is usually accomplished by passing the fabric web in front of a light box. The light from the light box enables an operator to detect a hole or other defect in the fabric. The operator then stops the line, repairs the defect and restarts the line. If the operator misses a defect, the defect may catch inside machinery during subsequent finishing or end up in a finished garment, which must be rejected. Since the cost of a defect increases substantially as more value is put into the fabric, the lowest cost place to find a defect is just after it has been made by the knitting machine. Unfortunately, inspectors are not infallible and, in addition, are only able to reliably inspect fabric moving less than about 80 yards per minute.

Various vision inspection systems have been attempted over the years but such systems have only been able to augment the operator and have not been able to inspect fabric without the intervention of the operator. Since the operator is tied to the inspection system, he is not able to operate more than one inspection station at the same time. If the inspection station did not require the operator's attention full time, the operator could move from one machine to another and make repairs to the fabric web as needed when the inspection system identified a defect and stopped the line.

Thus, there remains a need for an apparatus for inspecting a tubular knitted fabric wed at high speed without operator intervention while, at the same time, allows an operator to make repairs and re-start inspection easily.

SUMMARY OF THE INVENTION

The present invention is directed to a moving fabric web vision inspection system. The apparatus includes at least two electronic cameras on one side of the moving fabric web for measuring the light intensity of a predetermined area of the moving fabric web. A high frequency, backlight contrast panel on the other side of the moving fabric web provides reference point for the cameras to detect a defect. A controller connected to each of the electronic cameras generates a stop signal if the light intensity of the predetermined area of the moving fabric web deviates from a predetermined value. The predetermined value corresponds to a detected defect in the moving fabric web. Finally, a repair station downstream from the cameras allows an operator to repair a defect detected by the vision inspection system.

In the preferred embodiment, the cameras are directed at the fabric web at substantially the same field of vision "window" to improve detection reliability. In addition, the cameras are directed at the fabric web at between 20 and 0 degrees from normal to reduce the effect of "hourglassing" of the high-speed web.

The backlight panel includes at least one fluorescent tube and high frequency ballast connected to the fluorescent tube. In the preferred embodiment, the high frequency ballast connected to the fluorescent tube is operable at about 20 kHz. to reduce flicker error. The backlight panel also may include a translucent diffuser panel between the light panel and the moving fabric web.

The repair station includes an overhead frame, a tension roll, and a doff roll downstream from the tension roll. The tension roll includes a high friction surface for engaging the fabric web. The doff roll includes a low friction surface for allowing some slippage of the fabric web. Also, the doff roll includes an anti-backlash roll positioned between 45 and 90 degrees with respect to the downstream surface of the doff roll to control the discharge angle of the fabric web.

Accordingly, one aspect of the present invention is to provide a moving fabric web vision inspection system. The apparatus includes: at least two electronic cameras on one side of the moving fabric web for measuring the light intensity of a predetermined area of the moving fabric web; a contrast panel on the other side of the moving fabric web; and a controller connected to each of the electronic cameras for generating a stop signal if the light intensity of the predetermined area of the moving fabric web deviates from a predetermined value, the predetermined value corresponding to a detected defect in the moving fabric web.

Another aspect of the present invention is to provide a moving fabric web vision inspection system. The apparatus includes: at least two electronic cameras on one side of the moving fabric web for measuring the light intensity of a predetermined area of the moving fabric web; a high frequency, backlight contrast panel on the other side of the moving fabric web; and a controller connected to each of the electronic cameras for generating a stop signal if the light intensity of the predetermined area of the moving fabric web exceeds a predetermined value, the predetermined value corresponding to a detected defect in the moving fabric web.

Still another aspect of the present invention is to provide a moving fabric web vision inspection system. The apparatus includes: at least two electronic cameras on one side of the moving fabric web for measuring the light intensity of a predetermined area of the moving fabric web; a high frequency, backlight contrast panel on the other side of the moving fabric web; a controller connected to each of the electronic cameras for generating a stop signal if the light intensity of the predetermined area of the moving fabric web deviates from a predetermined value, the predetermined value corresponding to a detected defect in the moving fabric web; and a repair station downstream from the cameras for repairing a defect detected by the vision inspection system.

These and other aspects of the present invention will become apparent to those skilled in the art after a reading of the following description of the preferred embodiment when considered with the drawings.

DESCRIPTION OF THE PREFERRED EMBODIMENTS

Figure 1:
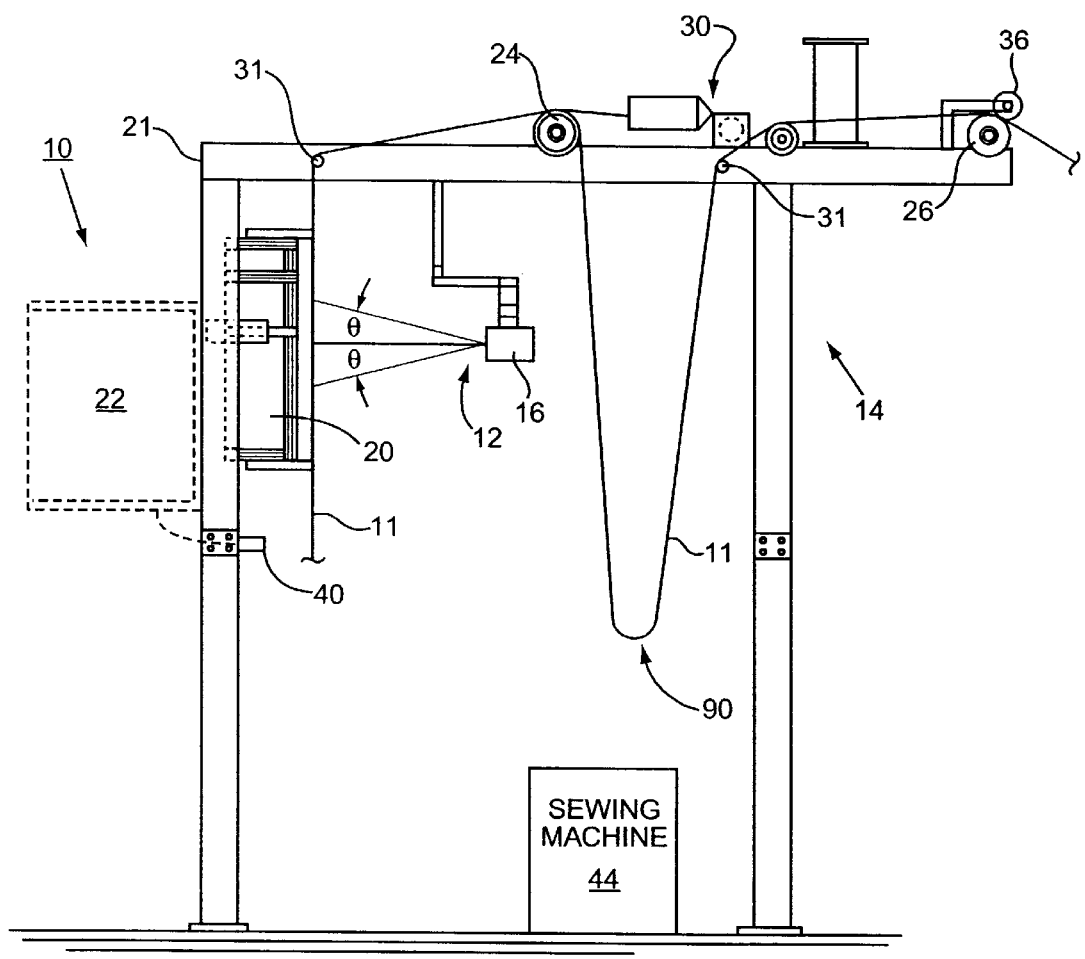
FIG. 1 is a side view of a fabric web vision inspection system and repair station constructed according to the present invention.
Figure 2:
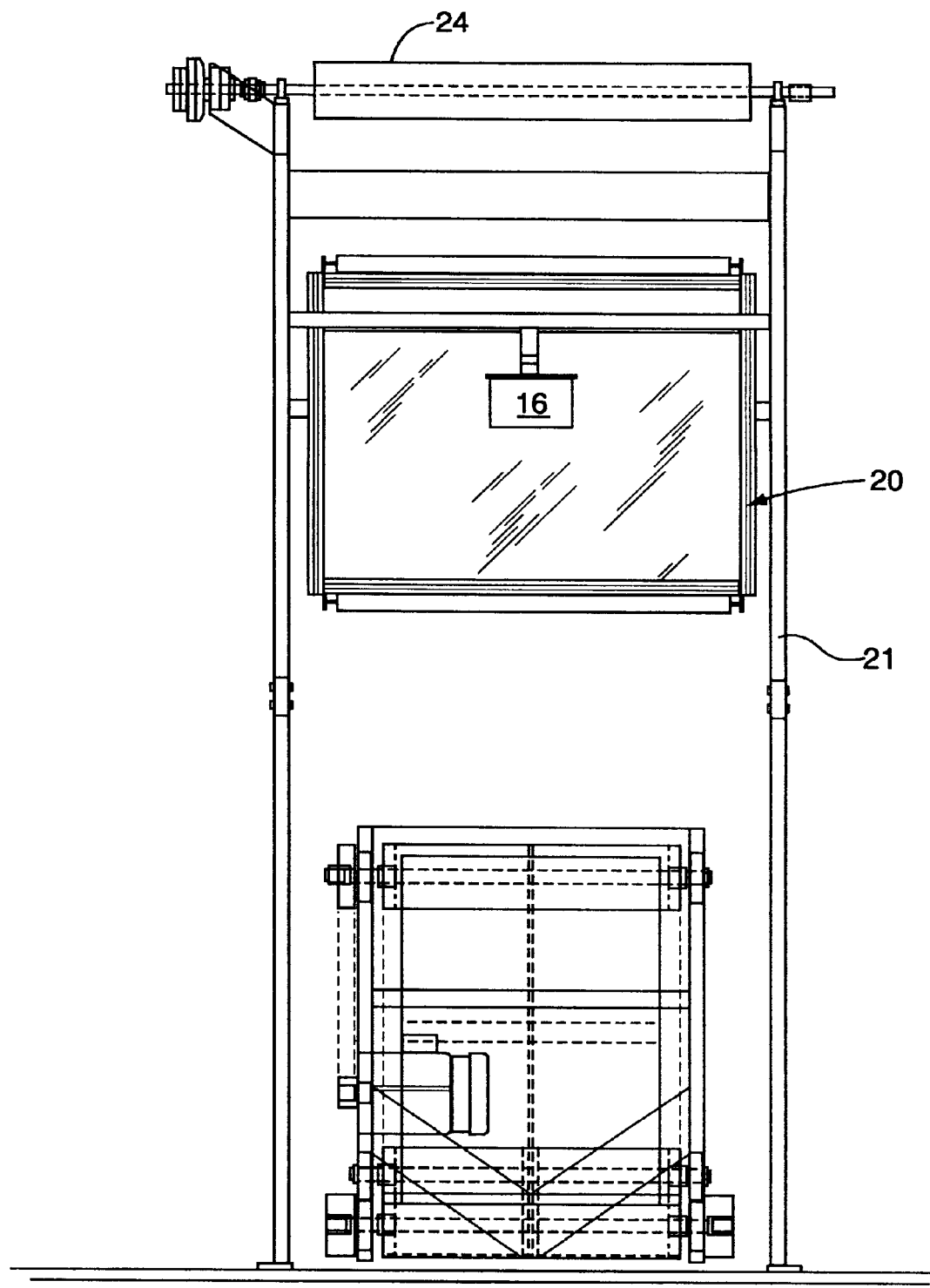
FIG. 2 is an enlarged front view of the vision inspection system.

In the following description, like reference characters designate like or corresponding parts throughout the several views. Also in the following description, it is to be understood that such terms as "forward", "rearward", "left", "right", "upwardly", "downwardly", and the like are words of convenience and are not to be construed as limiting terms.

Referring now to the drawings in general and FIG. 1 in particular, it will be understood that the illustrations are for the purpose of describing a preferred embodiment of the invention and are not intended to limit the invention thereto. As best seen in FIG. 1, an operator free fabric web inspection system, generally designated 10 is shown constructed according to the present invention. The fabric web inspection system 10 includes two major sub-assemblies: a vision system 12 for detecting a defect in the moving fabric web; and a repair station 14 downstream from the vision system for allowing an operator to repair the defect and restart the line.

The operator free fabric web inspection system 10 is used for inspecting continuous rolls of fabric. In one embodiment, the fabric is produced in large rolls of continuous fabric that may weigh in excess of 450 pounds which are then batched through the system using a large roll takeoff device such as that disclosed in co-pending U.S. patent application Ser. No. 08/911,296, filed Aug. 8, 1997, now U.S. Pat. No. 6,082,143, which is hereby incorporated by reference in its entirety. The large roll may be fed into the inspection system of the present invention using a roll letoff disclosed in co-pending U.S. patent application Ser. No. 09/260,174, filed Mar. 1, 1999, now U.S. Pat. No. 6,101,691 which is hereby incorporated by reference in its entirety. The present invention is also operable on numerous other types of fabric including knit, woven, and others.

Vision system 12 includes at least two cameras 16 aimed at a contrast panel 20 located on the opposite side of the moving fabric web. In the preferred embodiment, cameras 16 are line scan type digital cameras. In the most preferred embodiment, cameras 16 provide an analog voltage output proportional to the intensity of light passing through a predetermined "window" of the fabric. The utilization of a "smart" camera which provides analog voltage output, results in substantial simplification of the control circuit since the controller does not have to convert the intensity measurements into analog voltage, but can take the voltage directly from the camera. One such camera is a model HVS 256–135 available from TFE of France. Such a camera has sufficient sensitivity to detect light passing through defect free fabric (about 50–60 lumens) at a distance of about 100 inches, depending in part on the lens chosen. The camera is a video CCD array camera scanning at about 115 milliseconds.

Figure 4:
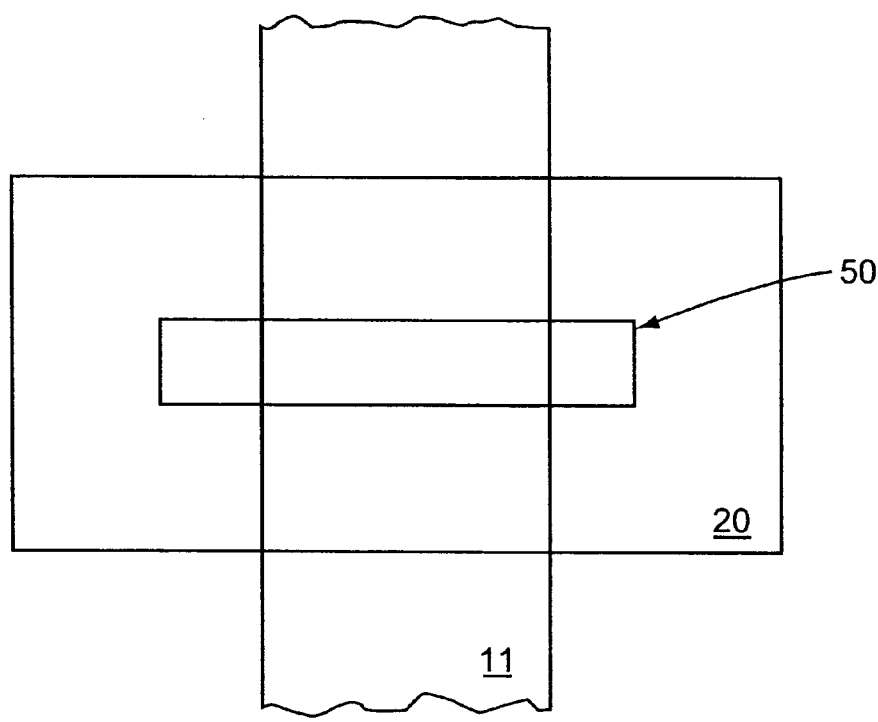
FIG. 4 is a front view of the moving fabric web as it passes in front of the backlight illustrating the field of vision of the cameras.

The cameras 16 monitor a field of vision, illustrated as 50 in FIG. 4, for a predetermined light intensity that is being emitted from the backlight 20. By way of example, cameras 16 are programmed to a set point such that a relative light intensity passing through the fabric of 50–60 lumens indicates a defect-free fabric. A defect in the fabric 11 causes the cameras 16 to monitor a light intensity either above or below this predetermined range. A hole in the fabric will allow more light to pass through the fabric causing a higher light intensity, and a thickness error will allow less light to pass causing a lower light intensity. The allowable light intensity range is adjustable depending upon the type of fabric being monitored.

In the preferred embodiment, each camera 16 is set to look at the same "window" of the moving fabric web. When the fabric was moving at about 200 yards per minute (10 ft/sec.), it was discovered that the response time of the camera was still more than fast enough to detect a defect passing through its field of view. However, the probability of a single camera detecting a known defect was not good enough for reliable detection rates. Thus, if the probability of detecting a defect could be improved, the speed of the line could be increased to between about 400 and 500 yards per minute or more! Various camera arrangements were tried or considered as shown below in Table 1. Values are shown on a 1–5 scale with 1 being low and 5 being high.

TABLE 1

| Example | Camera Arrangement | Response Time | Defect Detection Probability |
|---------|--------------------|---------------|------------------------------|
| 1 | Single | 5 | 2 |
| 2 | Side-by-Side | 5 | 2 |
| 3 | Over and Under | 5 | 3 |
| 4 | Dual/Same Window | 5 | 5 |

As can be seen, reducing the field of view of the camera and adding a second camera beside the first camera viewing only half the fabric web did not improve the probability since each camera was, as stated above, apparently was already fast enough. In addition, over and under field of view produced false stops since the surface texture of the fabric in the field of view changes as it moves. However, the dual camera, same window arrangement produced excellent results.

In the preferred embodiment, the cameras 16 monitor their field of vision, illustrated as 50 in FIG. 4, for a predetermined light intensity that is being emitted from a backlight 20. Again, by way of example, cameras 16 are programmed to a set point such that a relative light intensity passing through the fabric of 50–60 lumens indicates a defect-free fabric. A defect in the fabric 11 causes the cameras 16 to monitor a light intensity either above or below this predetermined range. A hole in the fabric will allow more light to pass through the fabric causing a higher light intensity, and a thickness error will allow less light to pass causing a lower light intensity. The allowable light intensity range is adjustable depending upon the type of fabric being monitored.

Also, in the preferred embodiment, each camera 16 is set to look substantially perpendicular at the same "window" of the moving fabric web. When the fabric was moving at high speeds, it was discovered that the fabric tended to "hourglass" which may cause a false stop since the cameras may believe that a defect passed through its field of view. However, when the position of the camera is moved closer to perpendicular to "hourglass" is reduced and the probability of detecting a false defect is lowered. Various camera angles were tried or considered as shown below in Table 2. Values are shown on a 1–5 scale with 1 being low and 5 being high.

TABLE 2

| Example | Camera Arrangement (degrees) | False Defect Avoidance |
| --- | --- | --- |
| 5 | 30 | 1 |
| 6 | 20 | 3 |
| 7 | 10 | 4 |
| 8 | 0 | 5 |

As can be seen, angles about 20 degrees or less from normal produced acceptable results with 0 degrees (perpendicular) producing the best results in avoiding the hourglass phenomena sometimes present in a high speed fabric web movement.

Figure 5:
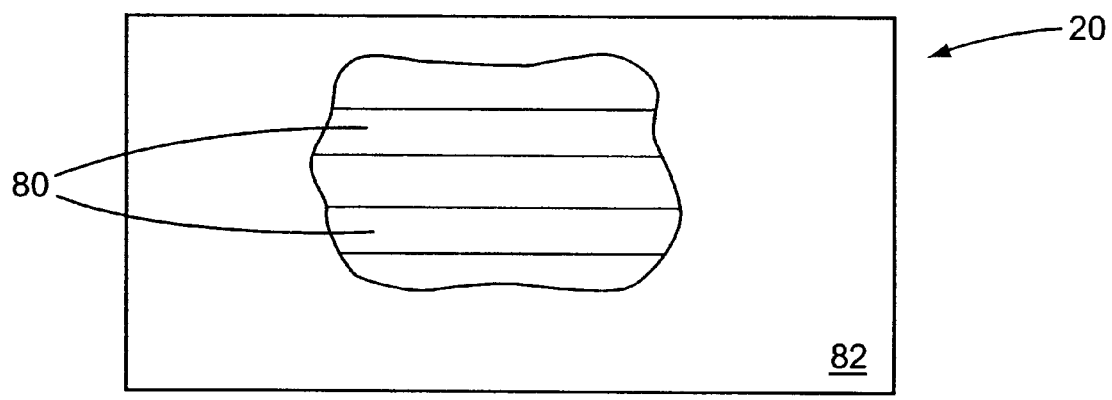
FIG. 5 is a front view of the backlight having a cutaway to illustrate the high frequency fluorescent tubes.

In order to make accurate measurements of the intensity of the light passing through the moving fabric web, it is necessary that there by a contrast between the moving fabric web and a reference. For a single color fabric, any contrasting surface behind the moving fabric web would be sufficient. However, finished fabric webs may be of any color from bleached white to bright red to black. Accordingly, in the preferred embodiment of the present invention, contrast panel is a backlight panel 20. As best seen in FIG. 5, the backlight panel 20 includes at least one fluorescent tube 80 for providing a reference light source. In addition, it has been found because of the speed of the moving fabric web and the sampling rate of the camera, conventional fluorescent ballast will produce a flicker, which may result in errors in measurement. Accordingly, in the preferred embodiment of the present invention the ballast is replaced with a high frequency ballast of about 20-kilohertz. One suitable high frequency ballast is a Valmont P/NE240SR120. In addition, in the preferred embodiment, a diffuser panel 82 is mounted above the fluorescent tubes to further improve uniformity of the light source.

The tension roll 24 moves the fabric through the system. Preferably, the tension roll 24 is wider than the fabric width to ensure the entire width of the fabric contacts the roll. The tension roll 24 is further coated with a high friction surface, such as a felt a covering, to increase the amount of adhesion by the fabric to the roll to minimize slippage and increase the efficiency of the roll in moving the fabric.

A doff roll 26 is positioned downstream of the tension roll 24 to further move the fabric. The width of the doff roll is preferably larger than the fabric width to provide maximum contact with the fabric. A low friction surface, such as a rubber covering, is placed on the doff roll 26 to further assist in the function of the roll in moving the fabric. Guide rollers 31 may be positioned throughout the repair station 14 to further direct the fabric.

An anti-backlash roll 36 is positioned against the doff roll 26 to prevent fabric that has passed through the doff roll from becoming tangled. The anti-backlash roll presses against the doff roll and may be positioned at a number of locations relative to the doff roll depending upon the desired exit point of the fabric from the doff roll. By way of example as illustrated in FIG. 1, the anti-backlash roll 36 is positioned at a relative location defined as one o'clock, which results in the fabric 11 being discharged at an angle below the contact point. When the anti-backlash roll is positioned further along the circumference of the doff roll, such as the four o'clock position, the fabric will remain on the doff roll for a longer period resulting in the exit point being beyond that position. The position of the anti-backlash roll functions to control the exit point of the fabric.

Figure 3:
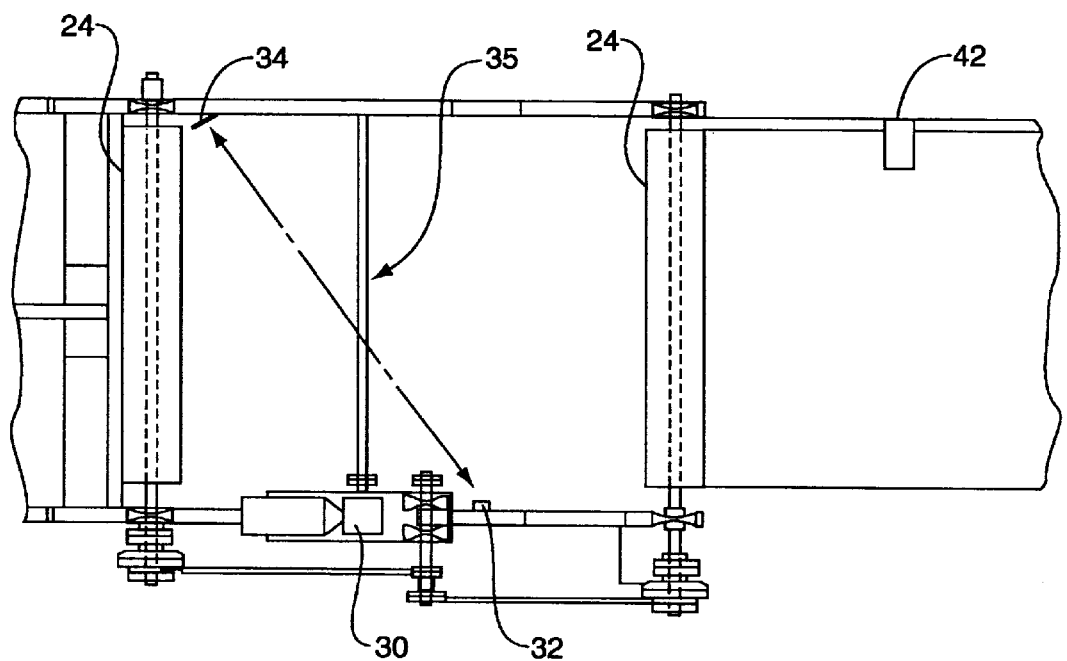
FIG. 3 is a top view of the present invention illustrating the tension roll and the doff roll.

The tension roll 24 and doff roll 26 are powered by drives that provide for both forward and backward rotation. In a preferred embodiment, the tension roll 24 and doff roll 26 are operated by the same drive 30 as illustrated in FIGS. 1 and 3. The drive 30 is equipped with individual clutches to allow for either only one of the rolls or both rolls to operate at a given time. In one embodiment, the drive is Model No. 3 hp AF4S3TC61Q1, manufactured by Lincoln.

A controller 22 monitors the inspection system and repair station to control the flow of fabric. The controller is programmable to provide for a number of settings for the various components depending upon the desired output. In one embodiment, the controller is a Model No. 405 having a D4-440 CPU, manufactured by Koyo Direct Logic, Inc., and scanning at between about 2 and 3 milliseconds (1 K boolean).

In operation, the fabric web is fed through the invention such that it passes between the cameras 16 and backlight 20, and over the tension roll 24 and the doff roll 26. The inspection system 12 is able to detect defects and the tension roll 24 and doff roll 26 are able to move the fabric more than about 500 yards per minute. It is expected that this rate may be further increased by dynamically balancing the rollers to allow for increased rpm's of the doff and tension rolls.

The output from the cameras 16 is sent to the controller 22 for determining the existence of a defect in the fabric. When a defect is detected by the controller 22, the controller shuts down the doff roll 26 and slows down the fabric feed into the system 10 and the rate of the tension roll 24. The fabric continues to feed into the system 10 and over the tension roll 24 for a predetermined time, and the controller then shuts both down to completely stop the movement of the fabric 11. During the predetermined period of time that the input feed and tension roll 24 continue to operate, the defect in fabric moves from the inspection station 12 to a point illustrated as 90 in FIG. 1. An operator monitoring the system may then take the fabric at point 90 and make the necessary repairs to correct the defect at sewing station 44. Once the repairs are completed, the operator restarts the system 10. The restart begins the doff roll 26 rotating at a slow speed to gather the fabric that has looped below.

An autostart sensor 35 is activated by the controller when a defect is detected to monitor the fabric that has looped to the sewing station. In one preferred embodiment, the autostart sensor includes a beam 32 and reflector 34 positioned as illustrated in FIG. 3 such that the beam is broken when fabric is looped to the sewing machine. Once the doff roll 26 takes up the looped fabric, the beam is no longer broken and a signal is sent to the controller indicating that all of the looped fabric has been fed through the doff roll resulting in the controller returning the fabric feeding into the system 10, the tension roll 24, and the doff roll 26 to again return to full operating speed.

A tail-out sensor 40 is positioned adjacent to the vision system 12 which signals the controller when there is no fabric feeding into the system 10 which results in the controller stopping the tension roll 24 and doff roll 26. Likewise, a downstream sensor 42 may be positioned downstream of the doff roll 26 when downstream processing is "log-jammed" and no further fabric may be fed through the system 10. Both the tail-out sensor 40 and downstream sensor 42 may include a beam and reflector, or other known detection devices.

Certain modifications and improvements will occur to those skilled in the art upon a reading of the foregoing description. It should be understood that all such modifications and improvements have been deleted herein for the sake of conciseness and readability but are properly within the scope of the following claims.

We claim:

1. A moving fabric web vision inspection system, said apparatus comprising:
   (a) at least two electronic cameras on one side of said moving fabric web for measuring the light intensity of a predetermined area of said moving fabric web;
   (b) a high frequency, backlight contrast panel on the other side of said moving fabric web; and
   (c) a controller connected to each of said electronic cameras for generating a stop signal if the light intensity of the predetermined area of said moving fabric web exceeds a predetermined value, said predetermined value corresponding to a detected defect in the moving fabric web.

2. The apparatus according to claim 1, wherein said cameras are directed at the fabric web at substantially the same field of vision window.

3. The apparatus according to claim 1, wherein said cameras are directed at the fabric web at between 20 and 0 degrees from normal.

4. The apparatus according to claim 3, wherein said cameras are directed at the fabric web at 0 degrees from normal.

5. The apparatus according to claim 1, wherein said backlight panel includes at least one fluorescent tube and a high frequency ballast connected to said fluorescent tube.

6. The apparatus according to claim 5, wherein said high frequency ballast connected to said fluorescent tube is operable at about 20 kHz.

7. The apparatus according to claim 1, wherein said backlight panel includes a translucent diffuser panel between said light panel and said moving fabric web.

8. The apparatus according to claim 1, wherein said controller has a scanning speed of between 2 and 3 milliseconds per 1 K Boolean.

9. The apparatus according to claim 1, further including a tail out sensor upstream from said vision inspection system for detecting the end of the fabric web.

10. The apparatus according to claim 1, further including a downstream sensor downstream from a doff roll for detecting a stoppage in the discharge of the fabric web.

* * * * *